US009200239B2

(12) United States Patent
Minning et al.

(10) Patent No.: US 9,200,239 B2
(45) Date of Patent: Dec. 1, 2015

(54) SAVINASE VARIANTS HAVING AN IMPROVED WASH PERFORMANCE ON EGG STAINS

(71) Applicant: Novozymes A/S, Bagsvaerd (DK)

(72) Inventors: Stefan Minning, Vienna (AT); Jurgen Carsten Franz Knotzel, Copenhagen (DK); Niels Henrik Sorensen, Skaevinge (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/296,693

(22) Filed: Jun. 5, 2014

(65) Prior Publication Data

US 2014/0287481 A1   Sep. 25, 2014

Related U.S. Application Data

(63) Continuation of application No. 13/555,504, filed on Jul. 23, 2012, which is a continuation of application No. 12/296,861, filed as application No. PCT/EP2007/053835 on Apr. 19, 2007, now abandoned.

(60) Provisional application No. 60/793,674, filed on Apr. 20, 2006.

(30) Foreign Application Priority Data

Apr. 20, 2006   (DK) ................. 2006 00543

(51) Int. Cl.
*C12N 9/50* (2006.01)
*C11D 3/386* (2006.01)
*C12N 15/11* (2006.01)

(52) U.S. Cl.
CPC ............ *C11D 3/386* (2013.01); *C11D 3/38627* (2013.01); *C11D 3/38636* (2013.01); *C11D 3/38645* (2013.01); *C11D 3/38654* (2013.01); *C12N 9/50* (2013.01)

(58) Field of Classification Search
None
See application file for complete search history.

(56) References Cited

U.S. PATENT DOCUMENTS

| 5,340,735 | A | 8/1994 | Christianson et al. |
|---|---|---|---|
| 5,453,372 | A | 9/1995 | Vetter et al. |
| 5,543,302 | A | 8/1996 | Boguslawski et al. |
| 5,801,039 | A | 9/1998 | Maurer et al. |
| 6,190,904 | B1 | 2/2001 | Amory et al. |
| 6,376,450 | B1 | 4/2002 | Ghosh et al. |
| 6,777,218 | B1 | 8/2004 | Mikkelsen et al. |
| 8,753,861 | B2 * | 6/2014 | Cascao-Pereira et al. .... 435/222 |
| 8,785,172 | B2 * | 7/2014 | Minning et al. ............. 435/221 |
| 2001/0044398 | A1 | 11/2001 | Speckmann et al. |
| 2005/0003985 | A1 | 1/2005 | Kottwitz et al. |
| 2005/0026269 | A1 | 2/2005 | Kottwitz et al. |
| 2011/0092408 | A1 * | 4/2011 | Draborg et al. ............. 510/226 |
| 2012/0149624 | A1 * | 6/2012 | Draborg et al. ............. 510/226 |

FOREIGN PATENT DOCUMENTS

| AU | 604640 | 2/1987 |
|---|---|---|
| EP | 130756 | 1/1985 |
| EP | 214435 | 3/1987 |
| EP | 251446 | 1/1988 |
| EP | 260105 | 3/1988 |
| WO | 87/04461 A1 | 7/1987 |
| WO | 87/05050 A1 | 8/1987 |
| WO | 88/08028 A1 | 10/1988 |
| WO | 88/08033 A1 | 10/1988 |
| WO | 89/06279 A1 | 7/1989 |
| WO | 91/00345 A1 | 1/1991 |
| WO | 94/02618 A1 | 2/1994 |
| WO | 95/10591 A1 | 4/1995 |
| WO | 95/23221 A1 | 8/1995 |
| WO | 95/27049 A1 | 10/1995 |
| WO | 95/29979 A1 | 11/1995 |
| WO | 95/30010 A1 | 11/1995 |
| WO | 95/30011 A2 | 11/1995 |
| WO | 01/44452 A1 | 6/2001 |
| WO | 01/68821 A1 | 9/2001 |
| WO | 01/75087 A1 | 10/2001 |
| WO | 2004/041979 A1 | 5/2004 |
| WO | 2004/099401 A1 | 11/2004 |
| WO | 2007/006305 A1 | 1/2007 |

OTHER PUBLICATIONS

Russel et al. J. Miol Biol, vol. 193, pp. 803-813 (1987).
Russel et al., Nature, vol. 328, pp. 496-500 (1987).
Thomas et al., Nature, vol. 318, pp. 375-376 (1985).

* cited by examiner

*Primary Examiner* — Manjunath Rao
*Assistant Examiner* — William Moore
(74) *Attorney, Agent, or Firm* — Kristin McNamara

(57) ABSTRACT

Subtilase variants having an improved wash performance on egg stains. These subtilases are useful exhibiting excellent or improved wash performance on egg stains when used in e.g. cleaning or detergent compositions, such as laundry detergent compositions and dish wash compositions, including automatic dish wash compositions.

7 Claims, 1 Drawing Sheet

```
No: 1         10        20        30        40        50
a) AQSVPYGVSQIKAPALHSQGYTGSNVKVAVIDSGIDSSHPDLKVAGGASM
b) AQSVPWGISRVQAPAAHNRGLTGSGVKVAVLDTGI*STHPDLNIRGGASF

No:           60        70        80        90       100
a) VPSETNPFQDNNSHGTHVAGTVAALNNSIGVLGVAPSASLYAVKVLGADG
b) VPGEPST*QDGNGHGTHVAGTIAALNNSIGVLGVAPSAELYAVKVLGASG

No:          110       120       130       140       150
a) SGQYSWIINGIEWAIANNMDVINMSLGGPSGSAALKAAVDKAVASGVVVV
b) SGSVSSIAQGLEWAGNNGMHVANLSLGSPSPSATLEQAVNSATSRGVLVV

No:          160       170       180       190       200
a) AAAGNEGTSGSSSTVGYPGKYPSVIAVGAVDSSNQRASFSSVGPELDVMA
b) AASGNSG*AGS***ISYPARYANAMAVGATDQNNNRASFSQYGAGLDIVA

No:          210       220       230       240       250
a) PGVSIQSTLPGNKYGAYNGTSMASPHVAGAAALILSKHPNWTNTQVRSSL
b) PGVNVQSTYPGSTYASLNGTSMATPHVAGAAALVKQKNPSWSNVQIRNHL

No:          260       270  275
a) ENTTTKLGDSFYYGKGLINVQAAAQ
b) KNTATSLGSTNLYGSGLVNAEAATR
```

SAVINASE VARIANTS HAVING AN IMPROVED WASH PERFORMANCE ON EGG STAINS

CROSS-REFERENCE TO RELATED APPLICATIONS

This application is a Continuation of U.S. Ser. No. 13/555,504 filed on Jul. 23, 2012 (now U.S. Pat. No. 8,785,172), which is a Continuation of U.S. Ser. No. 12/296,861 filed on Oct. 10, 2008, which is a 35 U.S.C. 371 national application of PCT/EP2007/053835 filed Apr. 19, 2007 which claims priority or the benefit under 35 U.S.C. 119 of Danish application no. PA 2006 00543 filed Apr. 20, 2006 and U.S. provisional application No. 60/793,674 filed Apr. 20, 2006, the contents of which are fully incorporated herein by reference.

TECHNICAL FIELD

The present invention relates to novel subtilases having an improved performance on soil, in particular egg stains. These subtilases are useful exhibiting excellent or improved performance on egg stains when used in e.g. cleaning or detergent compositions, such as laundry detergent compositions and dish wash compositions, including automatic dish wash compositions.

The present invention also relates to isolated polynucleotides encoding the subtilases, nucleic acid constructs, recombinant expression vectors, host cells comprising the nucleic acid construct, and methods for producing and using the subtilases of the invention. Further, the present invention relates to cleaning and detergent compositions comprising the subtilase enzymes of the invention as well as to use of such enzymes in detergent compositions and for removal of egg stains.

BACKGROUND OF THE INVENTION

In the detergent industry enzymes have for more than 30 years been implemented in washing formulations. Enzymes used in such formulations comprise proteases, lipases, amylases, cellulases, as well as other enzymes, or mixtures thereof. Commercially the most important enzymes are proteases.

An increasing number of commercially used proteases are protein engineered variants or naturally occurring wild type proteases, e.g. Relase®, Alcalase®, Savinase®, Primase®, Everlase®, Esperase®, Ovozyme®, Coronase®, Polarzyme® and Kannase® (Novozymes A/S), Maxatase™, Maxacal™, Maxapem™, Properase™, Purafect™, Purafect OxP™, FN2™, FN3™, FN4™ and Purafect Prime™ (Genencor International, Inc.), BLAP X and BLAP S (Henkel). Further, a number of protease variants are described in the art. A thorough list of prior art protease variants is given in WO 99/27082.

Further, a number of protease variants is described in the art, such as in EP 130 756; EP 214 435; WO 87/04461; WO 87/05050; EP 260 105; Thomas, Russell, and Fersht (1985) *Nature* 318:375-376; Thomas, Russell, and Fersht (1987) *J. Mol. Biol.* 193:803-813; Russel and Fersht *Nature* 328:496-500 (1987); WO 88/08028; WO 88/08033; WO 95/27049; WO 95/30011; WO 95/30010; WO 95/29979; U.S. Pat. No. 5,543,302; EP 251 446; WO 89/06279; WO 91/00345; EP 525 610; WO 94/02618.

WO 01/60963 describes detergent composition comprising variants of the *B. lentus* DSM 5843 alkaline protease having substitution(s) in at least one of the positions 3, 4, 99, 188, 193, 199 and 211, where the only examplified variant is S3T+V4I+V193M+V199I+L211D. It is disclosed that these variants shows an unexpecteed synergistic effect in combination with certain peroxidic oxidation agents.

WO 02/088340 describes a variant of the *B. lentus* DSM 5843 alkaline protease having the modifications S3T+A4I+A199I+L211G. The variant shows improved performance in automatized dishwashing compared to wild type alkaline proteases.

WO 01/75087 describes subtilisin homologues that are improved for a variety of specific properties including thermal stability, activity at low temperature and alkaline stability. WO 01/68821 describes subtilase enzymes, which are suitable for removal of egg stains from for example laundry and/or hard surfaces. WO 2004/099401 describes subtilase enzymes, which are suitable for removal of egg stains from for example laundry and/or hard surfaces.

However, even though a number of useful proteases and protease variants have been described, there is still a need for further improvement of proteases or protease variants for a number of industrial uses. In particular, the problem of removing egg stains from e.g. laundry or hard surfaces has been pronounced due to the fact that substances present in the egg white inhibit many serine proteases. Therefore, an object of the present invention is to provide improved subtilase enzymes, which are suitable for removal of egg stains from for example laundry and/or hard surfaces.

SUMMARY OF THE INVENTION

Thus, in a first aspect the present invention relates to subtilase enzyme variants having improved wash performance on egg stains, the variants being derived from the parent subtilase Savinase by the Following Modifications:
(Savinase variant 1) S3T+V4I+S99D+S101R+S103A+V104I+G160S+V205I+L217D or
(Savinase variant 2) S3T+V4I+S99D+S101R+S103A+V104I+G160S+A194P+V205I+L217D.

Concerning alignment and numbering, reference is made to FIG. 1 which shows an alignment between subtilisin BPN' (a) (BASBPN) and subtilisin 309 (b) (BLSAVI). This alignment is in this patent application used as a reference for numbering the residues.

DEFINITONS

Prior to discussing this invention in further detail, the following terms and conventions will first be defined.
Nomenclature and Conventions for Designation of Variants
In describing the various subtilase enzyme variants produced or contemplated according to the invention, the following nomenclatures and conventions have been adapted for ease of reference:

A frame of reference is first defined by aligning the isolated or parent enzyme with subtilisin BPN' (BASBPN). Such an alignment between subtilisin BPN' (BASBPN) and the parent subtilisin 309 is indicated in FIG. 1. A number of deletions and insertions are defined in relation to BASBPN. Deletions are in FIG. 1 indicated by asterixes (*).

The various modifications performed in a parent enzyme are indicated in general using three elements as follows:
Original Amino Acid Position Substituted Amino Acid
The notation G195E means a substitution of a glycine in position 195 with a glutamic acid.

Position Substituted Amino Acid

In the case where the original amino acid residue may be any amino acid residue, a short hand notation may at times be used indicating only the position and substituted amino acid: 170Ser or 170S. Such a notation is particular relevant in connection with modification(s) in homologous subtilases (vide infra).

Original Amino Acid Position

Such a notation is in particular relevant when the identity of the substituting amino acid residue(s) is immaterial. The substitution of any amino acid residue acid for glycine in position 195 is designated as: Gly195 or G195.

Position

When both the original amino acid(s) and substituted amino acid(s) may comprise any amino acid, then only the position is indicated, e.g.: 170.

Original Amino Acid Position {Substituted Amino Acid1 . . . Substituted Amino Acidn}

When the original amino acid(s) and/or substituted amino acid(s) may comprise more than one, but not all amino acid(s), then the selected amino acids are indicated inside brackets: { }.

For specific variants the specific three or one letter codes are used, including the codes Xaa and X to indicate any amino acid residue.

Substitutions:

The substitution of Glutamic acid for glycine in position 195 is designated as: Gly195Glu or G195E. The substitution of any amino acid residue acid for glycine in position 195 is designated as: Gly195Xaa or G195X, or Gly195 or G195. The substitution of serine for any amino acid residue in position 170 would thus be designated: Xaa170Ser or X170S, or 170Ser or 170S.

Such a notation is particular relevant in connection with modification(s) in homologous subtilases (vide infra). 170Ser is thus meant to comprise e.g. both a Lys170Ser modification in BASBPN and Arg170Ser modification in the subtilase according to the invention (cf. FIG. 1).

For a modification where the original amino acid(s) and/or substituted amino acid(s) may comprise more than one, but not all amino acid(s), the substitution of glycine, alanine, serine or threonine for arginine in position 170 would be indicated by: Arg170{Gly,Ala,Ser,Thr} or R170{G,A,S,T} to indicate the variants R170G, R170A, R170S, and R170T.

Deletions:

A deletion of glycine in position 195 will be indicated by: Gly195* or G195*. Correspondingly, the deletion of more than one amino acid residue, such as the deletion of glycine and leucine in positions 195 and 196 will be designated: Gly195*+Leu196* or G195*+L196*.

Insertions:

The insertion of an additional amino acid residue such as e.g. a lysine after G195 is indicated by: Gly195GlyLys or G195GK; or when more than one amino acid residue is inserted, such as e.g. a Lys, and Ala after G195 this will be indicated as: Gly195GlyLysAla or G195GKA.

In such cases, the inserted amino acid residue(s) are numbered by the addition of lower case letters to the position number of the amino acid residue preceding the inserted amino acid residue(s). In the above example, the sequences 194 to 196 would thus be:

|  | 194 | 195 | 195a | 195b | 196 |
|---|---|---|---|---|---|
| BLSAVI | A | - G | | | - L |
| Variant | A | - G | - K | - A | - L |

In cases where an amino acid residue identical to the existing amino acid residue is inserted it is clear that degeneracy in the nomenclature arises. If for example a glycine is inserted after the glycine in the above example this would be indicated by G195GG. The same actual change could just as well be indicated as A194AG for the change from

|  | 194 | 195 | 196 |
|---|---|---|---|
| BLSAVI to | A - | G - | L |

|  | 194 | 195 | 195a | 196 |
|---|---|---|---|---|
| Variant | A - | G - | G - | L |
|  | 194 | 194a | 195 | 196 |

Such instances will be apparent to the skilled person, and the indication G195GG and corresponding indications for this type of insertions are thus meant to comprise such equivalent degenerate indications.

Filling a Gap:

Where a deletion in an enzyme exists in the reference comparison with the subtilisin BPN' sequence used for the numbering, an insertion in such a position is indicated as:
*36Asp or *36D for the insertion of an aspartic acid in position 36.

Multiple Modifications:

Variants comprising multiple modifications are separated by pluses, e.g.:
Arg170Tyr+Gly195Glu or R170Y+G195E representing modifications in positions 170 and 195 substituting tyrosine and glutamic acid for arginine and glycine, respectively.

Thus, Tyr167{Gly,Ala,Ser,Thr}+Arg170{Gly,Ala,Ser,Thr} designates the following variants:
Tyr167Gly+Arg170Gly, Tyr167Gly+Arg170Ala,
Tyr167Gly+Arg170Ser, Tyr167Gly+Arg170Thr,
Tyr167Ala+Arg170Gly, Tyr167Ala+Arg170Ala,
Tyr167Ala+Arg170Ser, Tyr167Ala+Arg170Thr,
Tyr167Ser+Arg170Gly, Tyr167Ser+Arg170Ala,
Tyr167Ser+Arg170Ser, Tyr167Ser+Arg170Thr,
Tyr167Thr+Arg170Gly, Tyr167Thr+Arg170Ala,
Tyr167Thr+Arg170Ser, and Tyr167Thr+Arg170Thr.

This nomenclature is particular relevant relating to modifications aimed at substituting, replacing, inserting or deleting amino acid residues having specific common properties, such as residues of positive charge (K, R, H), negative charge (D, E), or conservative amino acid modification(s) of e.g. Tyr167{Gly,Ala,Ser,Thr}+Arg170{Gly,Ala,Ser,Thr}, which signifies substituting a small amino acid for another small amino acid. See the section "Detailed description of the invention" for further details.

Proteases

Enzymes cleaving the amide linkages in protein substrates are classified as proteases, or (interchangeably) peptidases (see Walsh, 1979, *Enzymatic Reaction Mechanisms. W.H. Freeman and Company, San Francisco*, Chapter 3).

Numbering of Amino Acid Positions/Residues

If nothing else is mentioned, the amino acid numbering used herein corresponds to that of the subtilase BPN' (BASBPN) sequence. For further description of the BPN' sequence, see FIG. 1 or Siezen et al., *Protein Engng.* 4 (1991) 719-737.

Serine Proteases

A serine protease is an enzyme which catalyzes the hydrolysis of peptide bonds, and in which there is an essential serine residue at the active site (White, Handler and Smith, 1973 *"Principles of Biochemistry,"* Fifth Edition, McGraw-Hill Book Company, NY, pp. 271-272).

The bacterial serine proteases have molecular weights in the 20,000 to 45,000 Dalton range. They are inhibited by diisopropyl fluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest (1977) *Bacteriological Rev.* 41:711-753).

Subtilases

Siezen et al have proposed a sub-group of the serine proteases tentatively designated subtilases, *Protein Engng,* 4 (1991) 719-737 and Siezen et al. *Protein Science* 6 (1997) 501-523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences reference is made to Siezen et al. (1997).

One subgroup of the subtilases, I—S1 or "true" subtilisins, comprises the "classical" subtilisins, such as subtilisin 168 (BSS168), subtilisin BPN' (BASBPN), subtilisin Carlsberg (BLSCAR or Alcalase®, Novozymes A/S), and subtilisin DY (BSSDY).

A further subgroup of the subtilases, I—S2 or high alkaline subtilisins, is recognized by Siezen et al. (supra). Subgroup I—S2 proteases are described as highly alkaline subtilisins and comprises enzymes such as subtilisin PB92 (BAALKP or Maxacal®, Genencor Inc.), subtilisin 309 (BLSAVI or Savinase®, Novozymes A/S), subtilisin 147 (BLS147 or Esperase®, Novozymes A/S), and alkaline elastase YaB (BSEYAB).

Parent Subtilase

The term "parent subtilase" describes a subtilase defined according to Siezen et al. (1991 and 1997). For further details, see description of "Subtilases" immediately above. A parent subtilase may also be a subtilase isolated from a natural source, wherein subsequent modifications have been made while retaining the characteristic of a subtilase. Furthermore, a parent subtilase may also be a subtilase which has been prepared by the DNA shuffling technique, such as described by J. E. Ness et al., *Nature Biotechnology,* 17:893-896 (1999). Alternatively the term "parent subtilase" may be termed "wild type subtilase". In the present case the parent subtilase of the subtilase variants of the invention is subtilisin 309.

Modification(s) of a Subtilase

The term "modification(s)" used herein is defined to include chemical modification of a subtilase as well as genetic manipulation of the DNA encoding a subtilase. The modification(s) can be replacement(s) of the amino acid side chain(s), substitution(s), deletion(s) and/or insertions in or at the amino acid(s) of interest.

Subtilase Variant

In the context of this invention, the term subtilase variant or mutated subtilase means a subtilase that has been produced by an organism which is expressing a mutant gene derived from a parent micro organism which possessed an original or parent gene and which produced a corresponding parent enzyme, the parent gene having been mutated in order to produce the mutant gene from which said mutated subtilase protease is produced when expressed in a suitable host. Analogously, the mutant gene may also be derived from a parent gene produced by DNA shuffling technique.

Isolated Polynucleotide

The term "isolated polynucleotide" as used herein refers to a polynucleotide, which has been isolated and purified and is thus in a form suitable for use within genetically engineered protein production systems. Such isolated molecules may be those that are separated from their natural environment and include cDNA and genomic clones as well as polynucleotides derived from DNA shuffling experiments or from site-directed autogenesis experiments. Isolated polynucleotides of the present invention are free of other genes with which they are ordinarily associated, but may include 5' and 3' untranslated regions such as promoters and terminators. The identification of associated regions will be evident to one of ordinary skill in the art (see for example Dynan and Tijan, *Nature* 316:774-78, 1985). The term "isolated nucleic acid sequence" may alternatively be termed "isolated DNA sequence", "cloned nucleic acid sequence" or "cloned DNA sequence".

Isolated Protein

When applied to a protein, the term "isolated" indicates that the protein has been removed from its native environment. In a preferred form, the isolated protein is substantially free of other proteins, particularly other homologous proteins (i.e. "homologous impurities" (see below)).

An isolated protein is more than 10% pure, preferably more than 20% pure, more preferably more than 30% pure, as determined by SDS-PAGE. Further, it is preferred to provide the protein in a highly purified form, i.e. more than 40% pure, more than 60% pure, more than 80% pure, more preferably more than 95% pure, and most preferably more than 99% pure, as determined by SDS-PAGE. The term "isolated protein" may alternatively be termed "purified protein".

Obtained From

The term "obtained from" as used herein in connection with a specific microbial source means that the polynucleotide and/or subtilase produced by the specific source, or by a cell in which a gene from the source has been inserted.

Substrate

The term "substrate" used in connection with a substrate for a protease should be interpreted in its broadest form as comprising a compound containing at least one peptide bond susceptible to hydrolysis by a subtilisin protease.

Product

The term "product" used in connection with a product derived from a protease enzymatic reaction should in the context of the present invention be interpreted to include the products of a hydrolysis reaction involving a subtilase protease. A product may be the substrate in a subsequent hydrolysis reaction.

Wash Performance

In the present context, the term "wash performance" is used as an enzyme's ability to remove soil, in particular egg stains present on the object to the cleaned during e.g. wash or hard surface cleaning. See also the "Model Detergent Wash Performance Test" in Example 2. A description of the AMSA test method for screening the wash performance of the enzyme can be found in WO 02/42740.

BRIEF DESCRIPTION OF THE DRAWINGS

FIG. 1 shows an alignment between subtilisin BPN' (*a*) (BASBPN) and subtilisin 309 (b) (BLSAVI) using the GAP routine mentioned above. This alignment is in this patent application used as a reference for numbering the residues.

DETAILED DESCRIPTION OF THE INVENTION

Thus, in a first aspect the present invention relates to subtilase enzyme variants having improved wash performance on egg stains, the variants being derived from the parent subtilase
Savinase by the Following Modifications:
(Savinase variant 1) S3T+V4I+S99D+S101R+S103A+V104I+G160S+V205I+L217D or
(Savinase variant 2) S3T+V4I+S99D+S101R+S103A+V104I+G160S+A194P+V205I+L217D.

In a second aspect the present invention relates to isolated polynucleotides comprising nucleic acid sequences encoding the subtilase variants according to the first aspect of the invention.

In a third aspect the present invention relates to a nucleic acid construct comprising the nucleic acid sequence according to the invention operably linked to one or more control sequences capable of directing the expression of the subtilase in a suitable host.

In a fourth aspect the present invention relates to a recombinant expression vector comprising the nucleic acid construct according to the invention, a promoter, and transcriptional and translational stop signals.

In a fifth aspect the present invention relates to a recombinant host cell comprising the nucleic acid construct of the invention.

In a sixth aspect the present invention relates to a method for producing the subtilase according to the invention, the method comprising:
(a) cultivating a recombinant host cell according to the invention under conditions conducive to the production of the subtilase; and
(b) recovering the subtilase.

In an seventh aspect the present invention relates to a cleaning or detergent composition, preferably a laundry or dish wash composition, comprising the subtilase according to the invention.

Further aspects of the present invention relate to use of the subtilases according to the invention in a cleaning or detergent composition; use of the subtilases or the compositions according to the invention for removal of egg stains; a method for cleaning or washing, including a method for removal of egg stains from a hard surface or laundry comprising contacting the hard surface or the laundry with the composition of the invention.

In another the subtilase variants of the present invention are combined with other modifications known in the art to provide improved properties to subtilases. The art describes a number of subtilase variants with different improved properties and a number of those is mentioned in the "Background of the invention" section herein (vide supra).

Such combinations comprise the positions: 222 (improves oxidation stability), 218 (improves thermal stability), substitutions in the $Ca^{2+}$-binding sites stabilizing the enzyme, e.g. position 76, and many other apparent from the prior art.

In further embodiments, a subtilase variant described herein may advantageously be combined with one or more modification(s) in any of the positions:
27, 36, 56, 76, 87, 95, 96, 97, 98, 100, 102, 120, 123, 159, 167, 170, 206, 218, 222, 224, 232, 235, 236, 245, 248, 252 and 274 (BPN' numbering).

Specifically, the following BLSAVI, BLSUBL, BSKSMK, and BAALKP modifications are considered appropriate for combination:
K27R, *36D, S56P, N76D, S87N, G97N, H120D, N123S, G159D, Y167, R170, Q206E, N218S, M222S, M222A, T224S, A232V, K235L, Q236H, Q245R, N248D, N252K and T274A.

Furthermore, variants comprising any combinations of the modifications K27R, N76D, S101G, S103A, V104N, V104Y, V104I, V104A, N123S, G159D, A232V, Q236H, Q245R, N248D, N252K, T274A; in particular K27R+N123S+T274A; in combination with any one or more of the modification(s) mentioned above exhibit improved properties.

A particular interesting variant is a variant, which in addition to modifications according to the invention contains the following substitutions:
G159D+A232V+Q236H+ Q245R+N248D+N252K.

Moreover, subtilase variants of the main aspect(s) of the invention are preferably combined with one or more modification(s) in any of the positions 129 and 131, preferably as 129K and 131H modifications, and most preferably as P129K and P131H modifications. Any of those modification(s) are expected to provide a higher expression level of the subtilase variant in the production thereof.

Furthermore, it is contemplated that insertion of at least one additional amino acid residue in the active site (b) loop region, corresponding to insertion of at least one additional amino acid residue from position 95 to position 103 (BASBPN numbering), will confer additional wash performance to the subtilase of the invention. In particular, it is preferred to insert at least one additional amino acid residue, such as one additional amino acid residue, in the following positions: between positions 98 and 99, and between positions 99 and 100.

Many methods for cloning a subtilase of the invention and for introducing insertions into genes (e.g. subtilase genes) are well-known in the art, cf. the references cited in the "BACKGROUND OF THE INVENTION" section.

In general standard procedures for cloning of genes and introducing insertions (random and/or site directed) into said genes may be used in order to obtain a subtilase enzyme of the invention. For further description of suitable techniques reference is made to Examples herein (vide infra) and (Sambrook et al. (1989) Molecular cloning: A laboratory manual, Cold Spring Harbor lab. Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for *Bacillus*". John Wiley and Sons, 1990); and WO 96/34946.

Further, a subtilase enzyme of the invention may be constructed by standard techniques for artificial creation of diversity, such as by DNA shuffling of different subtilase genes (WO 95/22625; Stemmer WPC, Nature 370:389-91 (1994)). DNA shuffling of e.g. the gene encoding Savinase® with one or more partial subtilase sequences identified in nature will, after subsequent screening for improved wash performance, provide subtilases according to the invention.

Polynucleotides

The present invention also relates to an isolated polynucleotide, which encodes a subtilase of the present invention, wherein the polynucleotide comprises nucleotides of SEQ ID NO:1 or of SEQ ID NO:3.

The present invention also encompasses polynucleotides that encode a polypeptide having the amino acid sequence of SEQ ID NO:2, which differ from SEQ ID NO:2 by virtue of the degeneracy of the genetic code; the present invention further encompasses polynucleotides that encode a polypeptide having the amino acid sequence of SEQ ID NO:4, which differ from SEQ ID NO:4 by virtue of the degeneracy of the genetic code. The present invention also relates to subsequences of SEQ ID NO:1 that encode fragments of SEQ ID NO:2 that have proteolytic activity, and to subsequences of SEQ ID NO:3 that encode fragments of SEQ ID NO:4 that have proteolytic activity.

A subsequence of SEQ ID NO:1 is a polynucleotide encompassed by nucleotides SEQ ID NO:1 except that one or more nucleotides from the 5' and/or 3' end have been deleted; a subsequence of SEQ ID NO:3 is a polynucleotide encompassed by nucleotides SEQ ID NO:3 except that one or more nucleotides from the 5' and/or 3' end have been deleted.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well-known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleic acid sequence-based amplification (NASBA) may be used.

An isolated polynucleotide can for example be obtained by standard cloning procedures used in genetic engineering to relocate the polynucleotide from its natural location to a different site where it will be reproduced. The cloning procedures may involve excision and isolation of a desired nucleic acid fragment comprising the polynucleotide encoding the subtilase, insertion of the fragment into a vector molecule, and incorporation of the recombinant vector into a host cell where multiple copies or clones of the polynucleotide will be replicated. The polynucleotide may be of genomic, cDNA, RNA, semi-synthetic, synthetic origin, or any combinations thereof.

For purposes of the present invention, the degree of identity between two polynucleotides is determined is described above.

Modification of a polynucleotide encoding a subtilase of the present invention may be necessary for the synthesis of subtilases substantially similar to the subtilase. The term "substantially similar" to the subtilase refers to non-naturally occurring forms of the subtilase. These subtilases may differ in some engineered way from the subtilase isolated from its native source, e.g., variants that differ in specific activity, thermostability, pH optimum, or the like. The variant sequence may be constructed on the basis of the polynucleotide presented as the polypeptide encoding part of SEQ ID NO:1, or on the basis of the polynucleotide presented as the polypeptide encoding part of SEQ ID NO:3, e.g., a subsequence thereof, and/or by introduction of nucleotide substitutions which do not give rise to another amino acid sequence of the subtilase encoded by the nucleic acid sequence, but which correspond to the codon usage of the host organism intended for production of the enzyme, or by introduction of nucleotide substitutions which may give rise to a different amino acid sequence. For a general description of nucleotide substitution see, e.g., Ford et al., 1991, Protein Expression and Purification 2: 95-107.

It will be apparent to those skilled in the art that such substitutions can be made outside the regions critical to the function of the molecule and still result in an active subtilase. Amino acid residues essential to the activity of the polypeptide encoded by the isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for proteolytic activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

Nucleic Acid Constructs

The present invention also relates to nucleic acid constructs comprising a polynucleotide of the present invention operably linked to one or more control sequences capable of directing the expression of the polypeptide in a suitable host cell.

An isolated polynucleotide encoding a subtilase of the present invention may be manipulated in a variety of ways to provide for expression of the subtilase. Manipulation of the polynucleotide prior to its insertion into a vector may be desirable or necessary depending on the expression vector. The techniques for modifying polynucleotides utilizing recombinant DNA methods are well-known in the art.

The control sequences include all components that are necessary or advantageous for the expression of a subtilase of the present invention. Each control sequence may be native or foreign to the polynucleotide encoding the subtilase. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a subtilase.

The control sequence may be an appropriate promoter sequence, a polynucleotide that is recognized by a host cell for expression of the nucleic acid sequence. The promoter sequence contains transcriptional control sequences that mediate the expression of the subtilase. The promoter may be any polynucleotide that shows transcriptional activity in the host cell of choice including mutant, truncated, and hybrid promoters, and may be obtained from genes encoding extracellular or intracellular subtilases either homologous or heterologous to the host cell.

Examples of suitable promoters for directing the transcription of the nucleic acid constructs of the present invention, especially in a bacterial host cell, are the promoters obtained from the E. coli lac operon, Streptomyces coelicolor agarase gene (dagA), Bacillus subtilis levansucrase gene (sacB), Bacillus licheniformis alpha-amylase gene (amyL), Bacillus stearothermophilus maltogenic amylase gene (amyM), Bacillus amyloliquefaciens alpha-amylase gene (amyQ), Bacillus licheniformis penicillinase gene (penP), Bacillus subtilis xylA and xylB genes, and prokaryotic beta-lactamase gene (VIIIa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25). Further promoters are described in "Useful proteins from recombinant bacteria" in Scientific American, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the polynucleotide encoding the subtilase. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Romanos et al., 1992, supra, describe other useful terminators for yeast host cells.

The control sequence may also be a suitable leader sequence, a non-translated region of an mRNA that is important for translation by the host cell. The leader sequence is operably linked to the 5' terminus of the polynucleotide encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the polynucleotide and which, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a subtilase and directs the encoded subtilase into the cell's secretory pathway. The 5' end of the coding sequence of the polynucleotide may inherently contain a signal peptide coding region naturally linked in translation reading frame with the segment of the coding region that encodes the secreted subtilase. Alternatively, the 5' end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the subtilase. However, any signal peptide coding region that directs the expressed subtilase into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Romanos et al., 1992, supra, describe other useful signal peptide coding regions.

The control sequence may also be a propeptide coding region that codes for an amino acid sequence positioned at the amino terminus of a subtilase. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a subtilase, the propeptide region is positioned next to the amino terminus of a subtilase and the signal peptide region is positioned next to the amino terminus of the propeptide region.

It may also be desirable to add regulatory sequences that allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus* niger glucoamylase promoter, and *Aspergillus oryzae* glucoamylase promoter may be used as regulatory sequences. Other examples of regulatory sequences are those that allow for gene amplification. In eukaryotic systems, these include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to a recombinant expression vector comprising the nucleic acid construct of the invention, a promoter, and transcriptional and translational stop signals.

The recombinant expression vector comprising the nucleic acid construct encoding the enzyme of the invention may be any vector that may conveniently be subjected to recombinant DNA procedures.

The choice of vector will often depend on the host cell into which it is to be introduced. Thus, the vector may be an autonomously replicating vector, i.e. a vector that exists as an extrachromosomal entity, the replication of which is independent of chromosomal replication, e.g. a plasmid. Alternatively, the vector may be one that on introduction into a host cell is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term "operably linked" indicates that the segments are arranged so that they function in concert for their intended purposes, e.g. transcription initiates in a promoter and proceeds through the DNA sequence coding for the enzyme.

The promoter may be any DNA sequence that shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gene, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host Cell

The present invention also relates to a recombinant host cell comprising the nucleic acid construct of the invention.

The DNA sequence encoding the present enzyme introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell that is capable of producing the present enzyme and includes bacteria, yeast, fungi and higher eukaryotic cells including plants.

Examples of bacterial host cells which on cultivation are capable of producing the enzyme of the invention are gram-positive bacteria such as strains of *Bacillus*, such as strains of *B. subtilis, B. licheniformis, B. lentus, B. brevis, B. stearothermophilus, B. alkalophilus, B. amyloliquefaciens, B. coagulans, B. circulans, B. lautus, B. megaterium* or *B. thuringiensis*, in particular *B. lentus*, or strains of *Streptomyces*, such as *S. lividans* or *S. murinus*, or gram-negative bacteria such as *Escherichia coli*.

The transformation of the bacteria may be effected by protoplast transformation, electroporation, conjugation, or by using competent cells in a manner known per se (cf. Sambrook et al., supra).

When expressing the enzyme in bacteria such as *E. coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in gram-positive bacteria such as *Bacillus* or *Streptomyces* strains, the enzyme may be retained in the cytoplasm, or may be directed to the extracellular medium by a bacterial secretion sequence. In the latter case, the enzyme may be recovered from the medium as described below.

In another embodiment of the invention, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology* and *Activities of Yeast* (Skinner, F. A., Passmore, S. M., and Davenport, R. R., eds., *Soc. App. Bacteriol. Symposium Series* No. 9, 1980).

In a preferred embodiment, the yeast host cell is a *Candida, Hansenula, Kluyveromyces, Pichia, Saccharomyces, Schizosaccharomyces,* or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium,* or *Trichoderma.*

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, *In* Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Method of Producing a Subtilase of the Invention

The present invention further relates to a method for producing a subtilase of the invention, the method comprising:
a) cultivating a recombinant host cell of the invention under conditions conducive to the production of the subtilase; and
b) recovering the subtilase.

When an expression vector comprising a DNA sequence encoding the enzyme is transformed into a heterologous host cell, it is possible to enable heterologous recombinant production of the enzyme of the invention.

Thereby it is possible to make a highly purified subtilase composition, characterized in being free from homologous impurities.

In this context, homologous impurities mean any impurities (e.g. other polypeptides than the enzyme of the invention) that originate from the homologous cell where the enzyme of the invention is originally obtained from.

The medium used to culture the transformed host cells may be any conventional medium suitable for growing the host cells in question. The expressed subtilase may conveniently be secreted into the culture medium and may be recovered there from by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

Use of a Subtilase of the Invention

A subtilase enzyme of the invention may be used for a number of industrial applications, in particular within the detergent industry. Thus, the present invention also relates to a cleaning or detergent composition, preferably a laundry or dish washing composition, comprising the subtilase enzyme of the invention.

Detergent Compositions Comprising the Subtilase Enzyme of the Invention:

In general, cleaning and detergent compositions are well described in the art and reference is made to WO 96/34946; WO 97/07202; WO 95/30011 for further description of suitable cleaning and detergent compositions.

Detergent Compositions

The enzyme of the invention may be added to and thus become a component of a detergent composition. The detergent composition of the invention may for example be formulated as a hand or machine laundry detergent composition including a laundry additive composition suiteble for pretreatment of stained fabrics and a rinse added fabric softener composition, or be formulated as a detergent composition for use in general household hard surface cleaning operations, or preferably be formulated for hand or machine dishwashing operations.

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases:

Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 68, 76, 87, 97, 101, 104, 106, 120, 123, 167, 170, 194, 206, 218, 222, 224, 235, 245, 252 and 274. Preferred commercially used protease enzymes include Relase®, Alcalase®, Savinase®, Primase®, Everlase®, Esperase®, Ovozyme®, Coronase®, Polarzyme® and Kannase® (Novozymes A/S), Maxatase™, Maxacal™, Maxapem™, Properase™, Purafect™, Purafect OxP™, FN2™, FN3™, FN4™ and Purafect Prime™ (Genencor International, Inc.), BLAP X and BLAP S (Henkel).

Lipases:

Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422). Other examples are lipase variants such as those described in WO 92/05249, WO 94/01541, EP 407225, EP 260105, WO 95/35381, WO 96/00292, WO 95/30744, WO 94/25578, WO 95/14783, WO 95/22615, WO 97/04079 and WO 97/07202. Preferred commercially used lipase enzymes include Lipolase®, Lipolase Ultra® and Lipex® (Novozymes A/S).

Amylases:

Suitable amylases ($\alpha$ and/or $\beta$) include those of bacterial or fungal origin. Chemically modified or protein engineered mutants are included. Amylases include, for example, $\alpha$-amylases obtained from *Bacillus*, e.g. a special strain of *B. licheniformis*, described in more detail in GB 1,296,839. Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially used amylases are Duramyl®, Termamyl®, Stainzyme®, Fungamyl® and BAN® (Novozymes A/S), Rapidase™, Purastar™ and Purastar OxAm™ (from Genencor International Inc.).

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259. Especially suitable cellulases are the alkaline or neutral cellulases having colour care and whiteness maintenance benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299. Commercially used cellulases include Renozyme®, Celluzyme®, and Carezyme® (Novozymes A/S), Clazinase™, and Puradax HA™ (Genencor Int. Inc.), and KAC-500(B)™ (Kao Corporation).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257. Commercially used peroxidases include Guardzyme™ (Novozymes A/S).

Hemicellulases:

Suitable hemicellulases include those of bacterial or fungal origin. Chemically modified or protein engineered mutants are included. Suitable hemicellulases include mannanase, lichenase, xylanase, arabinase, galactanase acetyl xylan esterase, glucorunidase, ferulic acid esterase, coumaric acid esterase and arabinofuranosidase as described in WO 95/35362. Suitable mannanases are described in WO 99/64619.

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethylene glycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste, a gel or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soilsuspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

SEQUENCE INFORMATION

SEQ ID NO:1—DNA sequence encoding Savinase variant 1,
SEQ ID NO:2—Amino acid sequence of Savinase variant 1,
SEQ ID NO:3—DNA sequence encoding Savinase variant 2,
SEQ ID NO:4—Amino acid sequence of Savinase variant 2,
SEQ ID NO:5—DNA sequence of the savinase variant S99SD+S99A, cf. WO 01/44452,
SEQ ID NO:6—Amino acid sequence of savinase variant S99SD+S99A, cf. WO 01/44452,
SEQ ID NO:7—DNA sequence of the savinase variant S99SD+S99A, cf. WO 01/44452,
SEQ ID NO:8—Amino acid sequence of savinase variant S99SD+S99A, cf. WO 01/44452,
SEQ ID NO:9—DNA sequence encoding *Bacillus lentus* alkaline protease—BLAP,
SEQ ID NO:10—Amino acid sequence of *Bacillus lentus* alkaline protease—BLAP,
SEQ ID NO:11—Amino acid sequence of *Bacillus amyloliquefaciens* protease—BPN',
SEQ ID NO: 12—Amino acid sequence of subtilisin 309—Savinase.

MATERIALS AND METHODS

Detergents

Detergents for wash performance tests of the proteases of the invention can be obtained by purchasing fully formulated commercial detergents at the market and subsequently inactivate the enzymatic components by heat treatment (5 minutes at 85° C. in aqueous solution). Moreover a commercial detergent base without enzymes can be purchased directly from the manufacturer. Further a suitable model detergent can be purchased and used for wash performance tests.

Textiles

Standard textile pieces are obtained from wfk-Cleaning Technology Research Institute, Christenfeld 10, D-41379 Brüggen-Bracht, Germany. Especially type wfk10N (cotton textile stained with egg/pigment).

Proteolytic Activity

In the context of this invention, proteolytic activity is expressed in Kilo NOVO Protease Units (KNPU). The activity is determined relatively to an enzyme standard (SAVINASE®), and the determination is based on the digestion of a dimethyl casein (DMC) solution by the proteolytic enzyme at standard conditions, i.e. 50° C., pH 8.3, 9 min. reaction time, 3 min. measuring time. A folder AF 220/1 is available upon request to Novozymes A/S, Denmark, which folder is hereby included by reference.

A GU is a Glycine Unit, defined as the proteolytic enzyme activity that under standard conditions during a 15 minutes' incubation at 40° C., with N-acetyl casein as substrate produces an amount of $NH_2$-group equivalent to 1 mmole of glycine.

Enzyme activity can also be measured using the PNA assay, according to reaction with the soluble substrate succinyl-alanine-alanine-proline-phenyl-alanine-para-nitro-phenol, which is described in the Journal of American Oil Chemists Society, Rothgeb, T. M., Goodlander, B. D., Garrison, P. H., and Smith, L. A., (1988).

Example 1

Construction and Expression of Subtilases According to the Invention

Example 1 covers both SEQ ID NO:2, and SEQ ID NO:4. It is to be understood that the term SEQ ID NO:2 at any time can be replaced by the term SEQ ID NO:4.

The subtilisin having the amino acid sequence shown in SEQ ID NO:2 was located in plasmid pKH400 (previously described in WO 98/41623). PKH400 was constructed from pJS3 (*E. coli—B. subtilis* shuttle vector containing a synthetic gene encoding for subtilase 309 (Savinase®) as described by J. Schiødt et al. in *Protein and Peptide Letters,* 3, 39-44 (1996)) by introduction of two BamHI sites at positions 1841 and 3730.

It includes an origin of replication for *E. coli* and *Bacillus*; the cat gene conferring resistance towards chloramphenicol, the promoter directing the initiation of transcription of the subtilisin and the pre/pro regions from Savinase®.

This plasmid replicates both in *E. coli* and in *Bacillus subtilis*, the subtilisins according to the invention was expressed from this plasmid in *Bacillus subtilis*. Fermentation and purification of the protease is described below.

Fermentation

Fermentations for the production of subtilase enzymes were performed at 30° C. on a rotary shaking table (300 rpm) in 500 ml baffled Erlenmeyer flasks containing 100 ml BPX medium for 5 days. Consequently, in order to make e.g. a 2 liter broth 20 Erlenmeyer flasks were fermented simultaneously.

BPX Medium Composition (per liter): Potato starch 100 g, Ground barley 50 g, Soybean flour 20 g, Na2HPO4·12 H2O 9 g, Dowfax® 63N10 (Dow Chemicals) 0.1 g, Sodium caseinate 10 g.

The starch in the medium was liquefied with α-amylase and the medium was sterilized by heating at 120° C. for 45 minutes. After sterilization the pH of the medium was adjusted to 9 by addition of $NaHCO_3$ to 0.1 M.

Purification

This procedure relates to purification of a 2 liter scale fermentation for the production of the subtilases of the invention in a *Bacillus* host cell.

Approximately 1.6 liters of fermentation broth was centrifuged at 5000 rpm for 35 minutes in 1 liter beakers. The supernatants were adjusted to pH 6.5 using 10% acetic acid and filtered on Seitz® Supra S100 filter plates (SeitzSchenk Filtersystems GmbH, Bad Kreuznach, DE).

The filtrates were concentrated to approximately 400 ml using an Amicon® CH2A UF unit equipped with an Amicon® S1Y10 UF cartridge (Millipore Corp. Billerica, Mass., USA). The UF concentrate was centrifuged and filtered at room temperature prior to absorption on a Bacitracin affinity column at pH 7. The subtilase was eluted from the Bacitracin column at room temperature using 25% 2-propanol and 1 M sodium chloride in a buffer solution with 0.01 dimethylglutaric acid, 0.1 M boric acid and 0.002 M calcium chloride adjusted to pH 7.

The fractions with protease activity from the Bacitracin purification step were combined and applied to a 750 ml Sephadex® G25 column (5 cm diameter) equilibrated with a buffer containing 0.01 dimethylglutaric acid, 0.2 M boric acid and 0.002 m calcium chloride adjusted to pH 6.5.

Fractions with proteolytic activity from the Sephadex® G25 column (Sigma-Aldrich Inc.) were combined and applied to a 150 ml CM Sepharose® CL 6B cation exchange column (5 cm diameter) (GE Healthcare/Amersham Biosciences) equilibrated with a buffer containing 0.01 M dimethylglutaric acid, 0.2 M boric acid, and 0.002 M calcium chloride adjusted to pH 6.5.

The protease was eluted using a linear gradient of 0-0.1 M sodium chloride in 2 liters of the same buffer. In a final purification step, protease-containing fractions from the CM Sepharose® column were combined and concentrated in an Amicon® ultra filtration cell equipped with a GR81PP membrane (from the Danish Sugar Factories Inc.).

By using the techniques mentioned above for the construction and fermentation, and the above isolation procedure, the novel subtilase having the amino acid sequence set forth in SEQ ID NO:2 was produced and isolated.

Example 2

Automatic Mechanical Stress Assay (AMSA)

Description of AMSA-Test Method:

Washing experiments are performed in order to asses the wash performance of selected protease variants in detergent compositions. The proteases of the present application are tested using the Automatic Mechanical Stress Assay (AMSA). With the AMSA, the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress in a regular, periodic oscillating manner. For further description see WO 02/42740 especially the paragraph "Special method embodiments" at page 23-24.

The experiment was conducted under the experimental conditions specified below:

| | |
|---|---|
| Commercial detergent base | Henkel Somat 3 in 1 |
| Detergent dosage | 5 g/L |
| Test solution volume | 160 micro L |
| pH | As is |
| Wash time | 20 minutes |
| Temperature | 55° C. |
| Water hardness | 16° dH |
| Enzyme concentration in test solution (nM) | a) 9.4; b) 18.8; c) 37.5; d) 94 nM |
| Test material | Wfk10N |

Water hardness was adjusted to 16° dH by addition of $CaCl_2$, $MgCl_2$, and $NaHCO_3$ ($Ca^{2+}:Mg^{2+}=4:1$) to the test system. After washing the textile pieces were flushed in tap water and dried.

The performance of the enzyme variant is measured as the brightness of the colour of the textile samples washed with that specific protease. Brightness can also be expressed as the intensity of the light reflected from the textile sample when illuminated with white light. When the textile is stained the intensity of the reflected light is lower, than that of a clean textile. Therefore the intensity of the reflected light can be used to measure wash performance of a protease.

Colour measurements are made with a professional flatbed scanner (PFU DL2400pro, obtainable from: J. M. Thomsen, Dorfgade 2, Dorf, Dronninglund, DK-9330), which is used to capture an image of the washed textile samples. The scans are made with a resolution of 200 dpi and with an output colour dept of 24 bits. In order to get accurate results, the scanner is frequently calibrated with a Kodak reflective IT8 target.

To extract a value for the light intensity from the scanned images, a special designed software application is used (Novozymes Color Vector Analyzer). The program retrieves the 24 bit pixel values from the image and converts them into values for red, green and blue (RGB). The intensity value (Int) is calculated by adding the RGB values together as vectors and then taking the length of the resulting vector:

$$Int = \sqrt{r^2 + g^2 + b^2}.$$

Textiles:

Standard textile pieces are obtained from wfk-Cleaning Technology Research Institute, Christenfeld 10, D-41379 Brüggen-Bracht, Germany. Especially type wfk10N (cotton textile stained with egg/pigment).

Using the above test method in combination with the commercially available detergent Somat 3 in 1 from Henkel KGaA gave the results shown in Table 1. The performance of the tested proteases is calculated relative to the performance two reference subtilases: Reference 1, the savinase variant S99SD+S99A disclosed in WO01/44452, and Reference 2, the *Bacillus lentus* alkaline protease-BLAP

TABLE 1

| Protease | Measured light intensity on textile treated with enzyme concentrations 0, a)-d) | | | | | Calculated relative performance of enzyme concentrations a)-d) | | | |
|---|---|---|---|---|---|---|---|---|---|
| | 0 | a) | b) | c) | d) | a) | b) | c) | d) |
| Reference 1 | 301 | 311.4 | 313.7 | 320.4 | 324.7 | 1.00 | 1.00 | 1.00 | 1.00 |
| Reference 2 | 301 | 312.3 | 316.3 | 320.2 | 324.6 | 1.09 | 1.20 | 0.99 | 1.00 |
| Savinase variant 1 | 301 | 326.7 | 332.6 | 336.6 | 341.1 | 2.47 | 2.49 | 1.84 | 1.69 |
| Savinase variant 2 | 301 | 327.3 | 333.3 | 337.9 | 339.8 | 2.53 | 2.54 | 1.90 | 1.64 |

As it appears, the subtilases according to the invention (SEQ ID NO:2 and SEQ ID NO:4) exhibits significantly improved wash performance on egg stains in comparison to the reference proteases.

Example 3

Microtiter Egg Assay (MEA)

In this assay the digestion of denatured egg proteins by proteases in the presence of detergent was followed in a 96-well microtiter plate. Heating of egg proteins produces visual changes and changes in physicochemical properties. The clear translucent material is transformed to a milky substance. This is partly due to sulfhydryl-disulfide interchange reactions of denatured proteins. For example, heating unmasks the sulfhydryl group of ovalbumin, and the unmasked groups form disulfide linkages. The digestion of the denatured egg proteins by proteases converts the milky egg solution to a more clear solution dependent on the ability of the enzymes to degrade egg proteins.

Procedure a) Make an egg solution of 200 mg egg powder (Sanovo International AS) and 93.7 mL 16° dH water. Denature the egg solution while the temperature increases to 85° C.;

b) Dilute the subtilase enzyme to 320 nM in succinic acid buffer: 10 mM succinic acid+2 mM $CaCl_2$+0.02% non-ionic detergent (such as Brij35 from Sigma-Aldrich) adjusted to pH 6.5;

c) Make the detergent solution just before use: 5 g detergent, such as a typical Western European Tablet detergent for automatic dishwashing, 937.5 mL water (16° dH($Ca^{2+}$/$Mg^{2+}$ 4:1));

d) Add to each well in a 96 well microtiter plate: 10 μl of 320 nM enzyme solution (final concentration 20 nM)+150 μl detergent solution (final concentration 5 g/L, 16° d)+egg solution (320 μg egg protein/well).

Measure OD 410 nm immediately (time 0 minutes) on a spectrophotometer. Incubate exactly 20 minutes at 55° C. and then measure OD 410 nm again. Calculate ΔOD (OD 0 minutes minus OD 20 minutes because the solution becomes less cloudy) and compare the variants with the performance of Reference 1. The performance of the reference is set to ΔOD=100%.

In Table 2 below are results obtained by use of the microtiter egg assay. Each run contained four identical replicates of each enzyme.

TABLE 2

| | Blank | Reference 1 | Savinase variant 1 | Savinase variant 2 |
|---|---|---|---|---|
| 1. run | | | | |
| Delta OD | 0.132 | 0.201 | 0.255 | 0.249 |
| Standard deviation | 0.02 | 0.01 | 0.02 | 0.02 |
| Delta OD minus blank | 0.000 | 0.068 | 0.122 | 0.117 |
| 2. run | | | | |
| Delta OD | 0.138 | 0.228 | 0.298 | 0.311 |
| Standard deviation | 0.02 | 0.01 | 0.02 | 0.02 |
| Delta OD minus blank | 0.000 | 0.091 | 0.160 | 0.173 |
| Average of two runs | | 0.079 | 0.141 | 0.145 |
| Performance in % of Reference 1 | | 100 | 178 | 183 |

The results clearly show that the subtilase variants of the invention exhibits improved degradation of egg-proteins in a detergent solution.

The invention claimed is:

1. An isolated polynucleotide encoding a subtilase, selected from the group consisting of
the polynucleotide of SEQ ID NO:1 and the polynucleotide of SEQ ID NO:3.

2. A nucleic acid construct comprising the nucleic acid sequence of claim 1 operably linked to one or more control sequences capable of directing the expression of the subtilase in a suitable host.

3. A recombinant expression vector comprising the nucleic acid construct of claim 2, a promoter, and transcriptional and translational stop signals.

4. A recombinant host cell comprising the nucleic acid construct of claim 2 or the expression vector of claim 3.

5. The host cell according to claim 4, which is a bacterium.

6. The host cell according to claim 4, which is a fungus or yeast.

7. A method for producing a subtilase, the method comprising:
(a) cultivating a recombinant host cell as defined in claim 4 under conditions conducive to the production of the subtilase; and
(b) recovering the subtilase.

* * * * *

SEQUENCE LISTING

<160> NUMBER OF SEQ ID NOS: 12

<210> SEQ ID NO 1
<211> LENGTH: 807
<212> TYPE: DNA
<213> ORGANISM: Artificial sequence
<220> FEATURE:
<223> OTHER INFORMATION: Variant
<220> FEATURE:
<221> NAME/KEY: CDS
<222> LOCATION: (1)..(807)

<400> SEQUENCE: 1

```
gcg caa acg ata cca tgg gga att agc cgt gtg caa gcc cca gct gcc      48
Ala Gln Thr Ile Pro Trp Gly Ile Ser Arg Val Gln Ala Pro Ala Ala
1               5                   10                  15 cat aac cgt gga ttg aca ggt tct ggt gta aaa gtt gct gtc ctc gat      96
```

His Asn Arg Gly Leu Thr Gly Ser Gly Val Lys Val Ala Val Leu Asp
            20                  25                  30 aca ggg ata tcc act cat cca gat cta aat att cgt ggt ggc gca agc    144
Thr Gly Ile Ser Thr His Pro Asp Leu Asn Ile Arg Gly Gly Ala Ser
        35                  40                  45 ttt gta cca ggg gaa ccg tcg act caa gat ggg aat ggg cat ggc acg    192
Phe Val Pro Gly Glu Pro Ser Thr Gln Asp Gly Asn Gly His Gly Thr
 50                  55                  60 cat gtg gcc ggg acg atc gct gct tta aac aat tcg att ggc gtt ctt    240
His Val Ala Gly Thr Ile Ala Ala Leu Asn Asn Ser Ile Gly Val Leu
 65                  70                  75                  80 ggc gta gct cct agc gct gag cta tac gct gtt aaa gtc cta ggg gcg    288
Gly Val Ala Pro Ser Ala Glu Leu Tyr Ala Val Lys Val Leu Gly Ala
                 85                  90                  95 gat ggt aga ggt gcg atc agc tcg att gcc caa gga ttg gaa tgg gca    336
Asp Gly Arg Gly Ala Ile Ser Ser Ile Ala Gln Gly Leu Glu Trp Ala
            100                 105                 110 ggg aac aat ggc atg cac gtt gct aat ttg agt tta gga agc cct tcg    384
Gly Asn Asn Gly Met His Val Ala Asn Leu Ser Leu Gly Ser Pro Ser
        115                 120                 125 cca agt gcc aca ctc gag caa gct gtt aat agc gcg act tct aga ggc    432
Pro Ser Ala Thr Leu Glu Gln Ala Val Asn Ser Ala Thr Ser Arg Gly
130                 135                 140 gtt ctt gtt gta gcg gca tct ggg aat tca ggt gca tcc tca atc agc    480
Val Leu Val Val Ala Ala Ser Gly Asn Ser Gly Ala Ser Ser Ile Ser
145                 150                 155                 160 tat ccg gcg cgc tat gcg aac gca atg gca gtc gga gct act gat caa    528
Tyr Pro Ala Arg Tyr Ala Asn Ala Met Ala Val Gly Ala Thr Asp Gln
                165                 170                 175 aac aac aac cgc gct agc ttt tca cag tat ggc gca ggc ctt gac att    576
Asn Asn Asn Arg Ala Ser Phe Ser Gln Tyr Gly Ala Gly Leu Asp Ile
            180                 185                 190 gtc gca ccc ggg gta aac att cag agc aca tac cca ggt tca aca tat    624
Val Ala Pro Gly Val Asn Ile Gln Ser Thr Tyr Pro Gly Ser Thr Tyr
        195                 200                 205 gcc agc gac aac ggt aca tcg atg gct act cct cat gtt gca ggc gcg    672
Ala Ser Asp Asn Gly Thr Ser Met Ala Thr Pro His Val Ala Gly Ala
210                 215                 220 gcc gcc ctt gtt aaa caa aag aac cca tct tgg tct aat gta caa att    720
Ala Ala Leu Val Lys Gln Lys Asn Pro Ser Trp Ser Asn Val Gln Ile
225                 230                 235                 240 cga aat cat cta aag aat acg gca act agt tta gga agc acg aac ttg    768
Arg Asn His Leu Lys Asn Thr Ala Thr Ser Leu Gly Ser Thr Asn Leu
                245                 250                 255 tat gga agc gga ctt gtt aac gca gaa gcg gca acg cgt                807
Tyr Gly Ser Gly Leu Val Asn Ala Glu Ala Ala Thr Arg
            260                 265

<210> SEQ ID NO 2
<211> LENGTH: 269
<212> TYPE: PRT
<213> ORGANISM: Artificial sequence
<220> FEATURE:
<223> OTHER INFORMATION: Synthetic Construct

<400> SEQUENCE: 2

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

-continued

```
Thr Gly Ile Ser Thr His Pro Asp Leu Asn Ile Arg Gly Gly Ala Ser
            35                  40                  45
Phe Val Pro Gly Glu Pro Ser Thr Gln Asp Gly Asn Gly His Gly Thr
 50                  55                  60
His Val Ala Gly Thr Ile Ala Ala Leu Asn Asn Ser Ile Gly Val Leu
 65                  70                  75                  80
Gly Val Ala Pro Ser Ala Glu Leu Tyr Ala Val Lys Val Leu Gly Ala
                 85                  90                  95
Asp Gly Arg Gly Ala Ile Ser Ser Ile Ala Gln Gly Leu Glu Trp Ala
            100                 105                 110
Gly Asn Asn Gly Met His Val Ala Asn Leu Ser Leu Gly Ser Pro Ser
        115                 120                 125
Pro Ser Ala Thr Leu Glu Gln Ala Val Asn Ser Ala Thr Ser Arg Gly
    130                 135                 140
Val Leu Val Val Ala Ala Ser Gly Asn Ser Gly Ala Ser Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Ala Gly Leu Asp Ile
            180                 185                 190
Val Ala Pro Gly Val Asn Ile Gln Ser Thr Tyr Pro Gly Ser Thr Tyr
        195                 200                 205
Ala Ser Asp Asn Gly Thr Ser Met Ala Thr Pro His Val Ala Gly Ala
    210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
            260                 265
```

<210> SEQ ID NO 3
<211> LENGTH: 807
<212> TYPE: DNA
<213> ORGANISM: Artificial sequence
<220> FEATURE:
<223> OTHER INFORMATION: Savinase variant 2
<220> FEATURE:
<221> NAME/KEY: CDS
<222> LOCATION: (1)..(807)

<400> SEQUENCE: 3

```
gcg caa acg ata cca tgg gga att agc cgt gtg caa gcc cca gct gcc    48
Ala Gln Thr Ile Pro Trp Gly Ile Ser Arg Val Gln Ala Pro Ala Ala
1               5                   10                  15 cat aac cgt gga ttg aca ggt tct ggt gta aaa gtt gct gtc ctc gat    96
His Asn Arg Gly Leu Thr Gly Ser Gly Val Lys Val Ala Val Leu Asp
            20                  25                  30 aca ggg ata tcc act cat cca gat cta aat att cgt ggt ggc gca agc   144
Thr Gly Ile Ser Thr His Pro Asp Leu Asn Ile Arg Gly Gly Ala Ser
        35                  40                  45 ttt gta cca ggg gaa ccg tcg act caa gat ggg aat ggg cat ggc acg   192
Phe Val Pro Gly Glu Pro Ser Thr Gln Asp Gly Asn Gly His Gly Thr
 50                  55                  60 cat gtg gcc ggg acg atc gct gct tta aac aat tcg att ggc gtt ctt   240
His Val Ala Gly Thr Ile Ala Ala Leu Asn Asn Ser Ile Gly Val Leu
 65                  70                  75                  80 ggc gta gct cct agc gct gag cta tac gct gtt aaa gtc cta ggg gcg   288
```

```
gat ggt aga ggt gcg atc agc tcg att gcc caa gga ttg gaa tgg gca      336
Asp Gly Arg Gly Ala Ile Ser Ser Ile Ala Gln Gly Leu Glu Trp Ala
                100                 105                 110 ggg aac aat ggc atg cac gtt gct aat ttg agt tta gga agc cct tcg      384
Gly Asn Asn Gly Met His Val Ala Asn Leu Ser Leu Gly Ser Pro Ser
            115                 120                 125 cca agt gcc aca ctc gag caa gct gtt aat agc gcg act tct aga ggc      432
Pro Ser Ala Thr Leu Glu Gln Ala Val Asn Ser Ala Thr Ser Arg Gly
        130                 135                 140 gtt ctt gtt gta gcg gca tct ggg aat tca ggt gca tcc tca atc agc      480
Val Leu Val Val Ala Ala Ser Gly Asn Ser Gly Ala Ser Ser Ile Ser
145                 150                 155                 160 tat ccg gcg cgc tat gcg aac gca atg gca gtc gga gct act gat caa      528
Tyr Pro Ala Arg Tyr Ala Asn Ala Met Ala Val Gly Ala Thr Asp Gln
                165                 170                 175 aac aac aac cgc gct agc ttt tca cag tat ggc cca ggc ctt gac att      576
Asn Asn Asn Arg Ala Ser Phe Ser Gln Tyr Gly Pro Gly Leu Asp Ile
            180                 185                 190 gtc gca ccc ggg gta aac att cag agc aca tac cca ggt tca aca tat      624
Val Ala Pro Gly Val Asn Ile Gln Ser Thr Tyr Pro Gly Ser Thr Tyr
        195                 200                 205 gcc agc gac aac ggt aca tcg atg gct act cct cat gtt gca ggc gcg      672
Ala Ser Asp Asn Gly Thr Ser Met Ala Thr Pro His Val Ala Gly Ala
210                 215                 220 gcc gcc ctt gtt aaa caa aag aac cca tct tgg tct aat gta caa att      720
Ala Ala Leu Val Lys Gln Lys Asn Pro Ser Trp Ser Asn Val Gln Ile
225                 230                 235                 240 cga aat cat cta aag aat acg gca act agt tta gga agc acg aac ttg      768
Arg Asn His Leu Lys Asn Thr Ala Thr Ser Leu Gly Ser Thr Asn Leu
                245                 250                 255 tat gga agc gga ctt gtt aac gca gaa gcg gca acg cgt                  807
Tyr Gly Ser Gly Leu Val Asn Ala Glu Ala Ala Thr Arg
            260                 265

<210> SEQ ID NO 4
<211> LENGTH: 269
<212> TYPE: PRT
<213> ORGANISM: Artificial sequence
<220> FEATURE:
<223> OTHER INFORMATION: Synthetic Construct

<400> SEQUENCE: 4

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
```

```
            115                 120                 125
Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Val Ala Pro Gly Val Asn Ile Gln Ser Thr Tyr Pro Gly Ser Thr Tyr
        195                 200                 205

Ala Ser Asp Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 5
<211> LENGTH: 810
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(810)

<400> SEQUENCE: 5 gcg caa tcg gta cca tgg gga att agc cgt gtg caa gcc cca gct gcc      48
Ala Gln Ser Val Pro Trp Gly Ile Ser Arg Val Gln Ala Pro Ala Ala
1               5                   10                  15 cat aac cgt gga ttg aca ggt tct ggt gta aaa gtt gct gtc ctc gat      96
His Asn Arg Gly Leu Thr Gly Ser Gly Val Lys Val Ala Val Leu Asp
            20                  25                  30 aca ggg ata tcc act cat cca gat cta aat att cgt ggt ggc gca agc     144
Thr Gly Ile Ser Thr His Pro Asp Leu Asn Ile Arg Gly Gly Ala Ser
        35                  40                  45 ttt gta cca ggg gaa ccg tcg act caa gat ggg aat ggg cat ggc acg     192
Phe Val Pro Gly Glu Pro Ser Thr Gln Asp Gly Asn Gly His Gly Thr
    50                  55                  60 cat gtg gcc ggg acg atc gct gct tta aac aat tcg att ggc gtt ctt     240
His Val Ala Gly Thr Ile Ala Ala Leu Asn Asn Ser Ile Gly Val Leu
65                  70                  75                  80 ggc gta gct cct agc gct gag cta tac gct gtt aaa gtc cta ggg gcc     288
Gly Val Ala Pro Ser Ala Glu Leu Tyr Ala Val Lys Val Leu Gly Ala
                85                  90                  95 gcc gac ggt tca ggt tcg gtc agc tcg att gcc caa gga ttg gaa tgg     336
Ala Asp Gly Ser Gly Ser Val Ser Ser Ile Ala Gln Gly Leu Glu Trp
            100                 105                 110 gca ggg aac aat ggc atg cac gtt gct aat ttg agt tta gga agc cct     384
Ala Gly Asn Asn Gly Met His Val Ala Asn Leu Ser Leu Gly Ser Pro
        115                 120                 125 tcg cca agt gcc aca ctc gag caa gct gtt aat agc gcg act tct aga     432
Ser Pro Ser Ala Thr Leu Glu Gln Ala Val Asn Ser Ala Thr Ser Arg
    130                 135                 140 ggc gtt ctt gtt gta gcg gca tct ggg aat tca ggt gca ggc tca atc     480
```

```
Gly Val Leu Val Val Ala Ala Ser Gly Asn Ser Gly Ala Gly Ser Ile
145                 150                 155                 160 agc tat ccg gcg cgc tat gcg aac gca atg gca gtc gga gct act gat      528
Ser Tyr Pro Ala Arg Tyr Ala Asn Ala Met Ala Val Gly Ala Thr Asp
                165                 170                 175 caa aac aac aac cgc gct agc ttt tca cag tat ggc gca ggc ctt gac      576
Gln Asn Asn Asn Arg Ala Ser Phe Ser Gln Tyr Gly Ala Gly Leu Asp
            180                 185                 190 att gtc gca ccc ggg gta aac gtg cag agc aca tac cca ggt tca aca      624
Ile Val Ala Pro Gly Val Asn Val Gln Ser Thr Tyr Pro Gly Ser Thr
        195                 200                 205 tat gcc agc tta aac ggt aca tcg atg gct act cct cat gtt gca ggt      672
Tyr Ala Ser Leu Asn Gly Thr Ser Met Ala Thr Pro His Val Ala Gly
    210                 215                 220 gcg gcc gcc ctt gtt aaa caa aag aac cca tct tgg tct aat gta caa      720
Ala Ala Ala Leu Val Lys Gln Lys Asn Pro Ser Trp Ser Asn Val Gln
225                 230                 235                 240 att cga aat cat cta aag aat acg gca act agt tta gga agc acg aac      768
Ile Arg Asn His Leu Lys Asn Thr Ala Thr Ser Leu Gly Ser Thr Asn
                245                 250                 255 ttg tat gga agc gga ctt gtt aac gca gaa gcg gca acg cgt              810
Leu Tyr Gly Ser Gly Leu Val Asn Ala Glu Ala Ala Thr Arg
            260                 265                 270

<210> SEQ ID NO 6
<211> LENGTH: 270
<212> TYPE: PRT
<213> ORGANISM: Artificial sequence
<220> FEATURE:
<223> OTHER INFORMATION: Synthetic Construct

<400> SEQUENCE: 6

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ala Asp Gly Ser Gly Ser Val Ser Ser Ile Ala Gln Gly Leu Glu Trp
            100                 105                 110

Ala Gly Asn Asn Gly Met His Val Ala Asn Leu Ser Leu Gly Ser Pro
        115                 120                 125

Ser Pro Ser Ala Thr Leu Glu Gln Ala Val Asn Ser Ala Thr Ser Arg
    130                 135                 140

Gly Val Leu Val Val Ala Ala Ser Gly Asn Ser Gly Ala Gly Ser Ile
145                 150                 155                 160

Ser Tyr Pro Ala Arg Tyr Ala Asn Ala Met Ala Val Gly Ala Thr Asp
                165                 170                 175

Gln Asn Asn Asn Arg Ala Ser Phe Ser Gln Tyr Gly Ala Gly Leu Asp
            180                 185                 190

Ile Val Ala Pro Gly Val Asn Val Gln Ser Thr Tyr Pro Gly Ser Thr
        195                 200                 205
```

```
Tyr Ala Ser Leu Asn Gly Thr Ser Met Ala Thr Pro His Val Ala Gly
        210                 215                 220

Ala Ala Ala Leu Val Lys Gln Lys Asn Pro Ser Trp Ser Asn Val Gln
225                 230                 235                 240

Ile Arg Asn His Leu Lys Asn Thr Ala Thr Ser Leu Gly Ser Thr Asn
                    245                 250                 255

Leu Tyr Gly Ser Gly Leu Val Asn Ala Glu Ala Ala Thr Arg
            260                 265                 270

<210> SEQ ID NO 7
<211> LENGTH: 810
<212> TYPE: DNA
<213> ORGANISM: Artificial sequence
<220> FEATURE:
<223> OTHER INFORMATION: Savinase variant from WO 01/44452
<220> FEATURE:
<221> NAME/KEY: CDS
<222> LOCATION: (1)..(810)

<400> SEQUENCE: 7 gcg caa tcg gta cca tgg gga att agc cgt gtg caa gcc cca gct gcc      48
Ala Gln Ser Val Pro Trp Gly Ile Ser Arg Val Gln Ala Pro Ala Ala
1               5                   10                  15 cat aac cgt gga ttg aca ggt tct ggt gta aaa gtt gct gtc ctc gat      96
His Asn Arg Gly Leu Thr Gly Ser Gly Val Lys Val Ala Val Leu Asp
            20                  25                  30 aca ggg ata tcc act cat cca gat cta aat att cgt ggt ggc gca agc     144
Thr Gly Ile Ser Thr His Pro Asp Leu Asn Ile Arg Gly Gly Ala Ser
        35                  40                  45 ttt gta cca ggg gaa ccg tcg act caa gat ggg aat ggg cat ggc acg     192
Phe Val Pro Gly Glu Pro Ser Thr Gln Asp Gly Asn Gly His Gly Thr
    50                  55                  60 cat gtg gcc ggg acg atc gct gct tta aac aat tcg att ggc gtt ctt     240
His Val Ala Gly Thr Ile Ala Ala Leu Asn Asn Ser Ile Gly Val Leu
65                  70                  75                  80 ggc gta gct cct agc gct gag cta tac gct gtt aaa gtc cta ggg gcc     288
Gly Val Ala Pro Ser Ala Glu Leu Tyr Ala Val Lys Val Leu Gly Ala
                85                  90                  95 gcc gac ggt tca ggt tcg gtc agc tcg att gcc caa gga ttg gaa tgg     336
Ala Asp Gly Ser Gly Ser Val Ser Ser Ile Ala Gln Gly Leu Glu Trp
            100                 105                 110 gca ggg aac aat ggc atg cac gtt gct aat ttg agt tta gga agc cct     384
Ala Gly Asn Asn Gly Met His Val Ala Asn Leu Ser Leu Gly Ser Pro
        115                 120                 125 tcg cca agt gcc aca ctc gag caa gct gtt aat agc gcg act tct aga     432
Ser Pro Ser Ala Thr Leu Glu Gln Ala Val Asn Ser Ala Thr Ser Arg
    130                 135                 140 ggc gtt ctt gtt gta gcg gca tct ggg aat tca ggt gca ggc tca atc     480
Gly Val Leu Val Val Ala Ala Ser Gly Asn Ser Gly Ala Gly Ser Ile
145                 150                 155                 160 agc tat ccg gcg cgc tat gcg aac gca atg gca gtc gga gct act gat     528
Ser Tyr Pro Ala Arg Tyr Ala Asn Ala Met Ala Val Gly Ala Thr Asp
                165                 170                 175 caa aac aac aac cgc gct agc ttt tca cag tat ggc gca ggc ctt gac     576
Gln Asn Asn Asn Arg Ala Ser Phe Ser Gln Tyr Gly Ala Gly Leu Asp
            180                 185                 190 att gtc gca ccc ggg gta aac gtg cag agc aca tac cca ggt tca aca     624
Ile Val Ala Pro Gly Val Asn Val Gln Ser Thr Tyr Pro Gly Ser Thr
        195                 200                 205 tat gcc agc tta aac ggt aca tcg atg gct act cct cat gtt gca ggt     672
```

```
Tyr Ala Ser Leu Asn Gly Thr Ser Met Ala Thr Pro His Val Ala Gly
            210                 215                 220 gcg gcc gcc ctt gtt aaa caa aag aac cca tct tgg tct aat gta caa    720
Ala Ala Ala Leu Val Lys Gln Lys Asn Pro Ser Trp Ser Asn Val Gln
225                 230                 235                 240 att cga aat cat cta aag aat acg gca act agt tta gga agc acg aac    768
Ile Arg Asn His Leu Lys Asn Thr Ala Thr Ser Leu Gly Ser Thr Asn
                245                 250                 255 ttg tat gga agc gga ctt gtt aac gca gaa gcg gca acg cgt            810
Leu Tyr Gly Ser Gly Leu Val Asn Ala Glu Ala Ala Thr Arg
            260                 265                 270

<210> SEQ ID NO 8
<211> LENGTH: 270
<212> TYPE: PRT
<213> ORGANISM: Artificial sequence
<220> FEATURE:
<223> OTHER INFORMATION: Synthetic Construct

<400> SEQUENCE: 8

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ala Asp Gly Ser Gly Ser Val Ser Ser Ile Ala Gln Gly Leu Glu Trp
            100                 105                 110

Ala Gly Asn Asn Gly Met His Val Ala Asn Leu Ser Leu Gly Ser Pro
        115                 120                 125

Ser Pro Ser Ala Thr Leu Glu Gln Ala Val Asn Ser Ala Thr Ser Arg
    130                 135                 140

Gly Val Leu Val Val Ala Ala Ser Gly Asn Ser Gly Ala Gly Ser Ile
145                 150                 155                 160

Ser Tyr Pro Ala Arg Tyr Ala Asn Ala Met Ala Val Gly Ala Thr Asp
                165                 170                 175

Gln Asn Asn Asn Arg Ala Ser Phe Ser Gln Tyr Gly Ala Gly Leu Asp
            180                 185                 190

Ile Val Ala Pro Gly Val Asn Val Gln Ser Thr Tyr Pro Gly Ser Thr
        195                 200                 205

Tyr Ala Ser Leu Asn Gly Thr Ser Met Ala Thr Pro His Val Ala Gly
    210                 215                 220

Ala Ala Ala Leu Val Lys Gln Lys Asn Pro Ser Trp Ser Asn Val Gln
225                 230                 235                 240

Ile Arg Asn His Leu Lys Asn Thr Ala Thr Ser Leu Gly Ser Thr Asn
                245                 250                 255

Leu Tyr Gly Ser Gly Leu Val Asn Ala Glu Ala Ala Thr Arg
            260                 265                 270

<210> SEQ ID NO 9
<211> LENGTH: 810
```

<212> TYPE: DNA
<213> ORGANISM: Bacillus lentus
<220> FEATURE:
<221> NAME/KEY: CDS
<222> LOCATION: (1)..(810)

<400> SEQUENCE: 9

```
gcg caa tcg gta cca tgg gga att agc cgt gtg caa gcc cca gct gcc       48
Ala Gln Ser Val Pro Trp Gly Ile Ser Arg Val Gln Ala Pro Ala Ala
1               5                   10                  15 cat aac cgt gga ttg aca ggt tct ggt gta aaa gtt gct gtc ctc gat       96
His Asn Arg Gly Leu Thr Gly Ser Gly Val Lys Val Ala Val Leu Asp
            20                  25                  30 aca ggg ata tcc act cat cca gat cta aat att cgt ggt ggc gca agc      144
Thr Gly Ile Ser Thr His Pro Asp Leu Asn Ile Arg Gly Gly Ala Ser
        35                  40                  45 ttt gta cca ggg gaa ccg tcg act caa gat ggg aat ggg cat ggc acg      192
Phe Val Pro Gly Glu Pro Ser Thr Gln Asp Gly Asn Gly His Gly Thr
    50                  55                  60 cat gtg gcc ggg acg atc gct gct tta aac aat tcg att ggc gtt ctt      240
His Val Ala Gly Thr Ile Ala Ala Leu Asn Asn Ser Ile Gly Val Leu
65                  70                  75                  80 ggc gta gct cct agc gct gag cta tac gct gtt aaa gtc cta ggg gcc      288
Gly Val Ala Pro Ser Ala Glu Leu Tyr Ala Val Lys Val Leu Gly Ala
                85                  90                  95 gcc gac ggt tca ggt tcg gtc agc tcg att gcc caa gga ttg gaa tgg      336
Ala Asp Gly Ser Gly Ser Val Ser Ser Ile Ala Gln Gly Leu Glu Trp
            100                 105                 110 gca ggg aac aat ggc atg cac gtt gct aat ttg agt tta gga agc cct      384
Ala Gly Asn Asn Gly Met His Val Ala Asn Leu Ser Leu Gly Ser Pro
        115                 120                 125 tcg cca agt gcc aca ctc gag caa gct gtt aat agc gcg act tct aga      432
Ser Pro Ser Ala Thr Leu Glu Gln Ala Val Asn Ser Ala Thr Ser Arg
    130                 135                 140 ggc gtt ctt gtt gta gcg gca tct ggg aat tca ggt gca ggc tca atc      480
Gly Val Leu Val Val Ala Ala Ser Gly Asn Ser Gly Ala Gly Ser Ile
145                 150                 155                 160 agc tat ccg gcg cgc tat gcg aac gca atg gca gtc gga gct act gat      528
Ser Tyr Pro Ala Arg Tyr Ala Asn Ala Met Ala Val Gly Ala Thr Asp
                165                 170                 175 caa aac aac aac cgc gct agc ttt tca cag tat ggc gca ggc ctt gac      576
Gln Asn Asn Asn Arg Ala Ser Phe Ser Gln Tyr Gly Ala Gly Leu Asp
            180                 185                 190 att gtc gca ccc ggg gta aac gtg cag agc aca tac cca ggt tca aca      624
Ile Val Ala Pro Gly Val Asn Val Gln Ser Thr Tyr Pro Gly Ser Thr
        195                 200                 205 tat gcc agc tta aac ggt aca tcg atg gct act cct cat gtt gca ggt      672
Tyr Ala Ser Leu Asn Gly Thr Ser Met Ala Thr Pro His Val Ala Gly
    210                 215                 220 gcg gcc gcc ctt gtt aaa caa aag aac cca tct tgg tct aat gta caa      720
Ala Ala Ala Leu Val Lys Gln Lys Asn Pro Ser Trp Ser Asn Val Gln
225                 230                 235                 240 att cga aat cat cta aag aat acg gca act agt tta gga agc acg aac      768
Ile Arg Asn His Leu Lys Asn Thr Ala Thr Ser Leu Gly Ser Thr Asn
                245                 250                 255 ttg tat gga agc gga ctt gtt aac gca gaa gcg gca acg cgt              810
Leu Tyr Gly Ser Gly Leu Val Asn Ala Glu Ala Ala Thr Arg
            260                 265                 270
```

<210> SEQ ID NO 10
<211> LENGTH: 270

<212> TYPE: PRT
<213> ORGANISM: Bacillus lentus

<400> SEQUENCE: 10

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ala Asp Gly Ser Gly Ser Val Ser Ser Ile Ala Gln Gly Leu Glu Trp
            100                 105                 110

Ala Gly Asn Asn Gly Met His Val Ala Asn Leu Ser Leu Gly Ser Pro
        115                 120                 125

Ser Pro Ser Ala Thr Leu Glu Gln Ala Val Asn Ser Ala Thr Ser Arg
    130                 135                 140

Gly Val Leu Val Val Ala Ala Ser Gly Asn Ser Gly Ala Gly Ser Ile
145                 150                 155                 160

Ser Tyr Pro Ala Arg Tyr Ala Asn Ala Met Ala Val Gly Ala Thr Asp
                165                 170                 175

Gln Asn Asn Asn Arg Ala Ser Phe Ser Gln Tyr Gly Ala Gly Leu Asp
            180                 185                 190

Ile Val Ala Pro Gly Val Asn Val Gln Ser Thr Tyr Pro Gly Ser Thr
        195                 200                 205

Tyr Ala Ser Leu Asn Gly Thr Ser Met Ala Thr Pro His Val Ala Gly
    210                 215                 220

Ala Ala Ala Leu Val Lys Gln Lys Asn Pro Ser Trp Ser Asn Val Gln
225                 230                 235                 240

Ile Arg Asn His Leu Lys Asn Thr Ala Thr Ser Leu Gly Ser Thr Asn
                245                 250                 255

Leu Tyr Gly Ser Gly Leu Val Asn Ala Glu Ala Ala Thr Arg
            260                 265                 270
```

<210> SEQ ID NO 11
<211> LENGTH: 275
<212> TYPE: PRT
<213> ORGANISM: B. amyloliquefaciens

<400> SEQUENCE: 11

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80
```

```
Val Leu Gly Val Ala Pro Ser Ala Ser Leu Tyr Ala Val Lys Val Leu
             85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
            130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
            195                 200                 205

Leu Pro Gly Asn Lys Tyr Gly Ala Tyr Asn Gly Thr Ser Met Ala Ser
            210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 12
<211> LENGTH: 269
<212> TYPE: PRT
<213> ORGANISM: Bacillus lentus

<400> SEQUENCE: 12

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175
```

-continued

```
Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```